United States Patent
Ellawand

(10) Patent No.: US 8,270,719 B2
(45) Date of Patent: Sep. 18, 2012

(54) GEM PATTERN MATCHING ALGORITHM TO DETERMINE THE PERCENTAGE MATCH OF A TARGET GEM PATTERN TO A DATABASE OF GEM PATTERNS

(75) Inventor: Mohamad Ellawand, Brooklyn, NY (US)

(73) Assignee: Gemological Appraisal Association, Inc., New York, NY (US)

( * ) Notice: Subject to any disclaimer, the term of this patent is extended or adjusted under 35 U.S.C. 154(b) by 871 days.

(21) Appl. No.: 12/287,834

(22) Filed: Oct. 14, 2008

(65) Prior Publication Data
US 2010/0092067 A1    Apr. 15, 2010

(51) Int. Cl.
*G06K 9/00* (2006.01)
(52) U.S. Cl. .......................... 382/181; 356/30
(58) Field of Classification Search .................... 356/30; 382/181
See application file for complete search history.

(56) References Cited

U.S. PATENT DOCUMENTS

| | | | | |
|---|---|---|---|---|
| 3,947,120 A | * | 3/1976 | Bar-Issac et al. | 356/30 |
| 5,124,935 A | * | 6/1992 | Wallner et al. | 347/225 |
| 7,239,739 B2 | * | 7/2007 | Lapa et al. | 382/141 |
| 2001/0006415 A1 | * | 7/2001 | Dinu et al. | 356/30 |

* cited by examiner

Primary Examiner — Kara E Geisel
(74) Attorney, Agent, or Firm — Leason Ellis LLP

(57) ABSTRACT

A method and gem pattern matching technique to analyze a target gemstone by analyzing a pattern created by transmitting a light source such as a laser beam through the gemstone to create a visual optical pattern and comparing the pattern to a database of known gemstone patterns to determine the percentage likelihood that the target gemstone will match a gemstone in the database. The matching is based on the weight of the heaviest spot in the pattern and its location in the gemstone image and comparing it to the weight and location of the heaviest spots in each gemstone image in the database to determine a percentage matching.

11 Claims, 6 Drawing Sheets

GEM PATTERN MATCHING ALGORITHM TO DETERMINE THE PERCENTAGE MATCH OF A TARGET GEM PATTERN TO A DATABASE OF GEM PATTERNS

BACKGROUND OF THE INVENTION

1. Field of the Invention

The present invention relates to the field of gem recognition by determining a specific pattern created by transmitting a beam of light such as from a laser beam into a gemstone and recording the refraction pattern emitted by the gemstone in order to identify a particular gemstone.

2. Description of the Prior Art

While techniques to determine a given refraction pattern of a gemstone are known in the prior art, the present inventor is not aware of any algorithm which utilizes a refraction pattern obtained from a specific gemstone and compares it to a database of refraction patterns of known gemstones to determine a percentage match of the target gemstone compared to the database of known patterns.

SUMMARY OF THE INVENTION

The present invention is a method and gem pattern matching technique to analyze a target gemstone by analyzing a pattern created by transmitting a light source such as a laser beam into the gemstone to create a refracted digital pattern and comparing that pattern to a database of known gemstone digital patterns to determine the percentage likelihood that the target gemstone will match a gemstone in the database. The matching is based on the area of the largest spot in each of 96 defined concentric, circular bands of the refracted digital pattern from the target gemstone and the clockwise angle of each of the identified largest spots relative to the designated origin angle in the target gemstone digital pattern and comparing the area and clockwise angle for each concentric band in the target gemstone digital pattern to the area and clockwise angle of the largest spots in each of the 96 concentric bands for each gemstone digital pattern in the database. Upon the occurrence of a match of the area and clockwise angle in a concentric band between the target gemstone and a database gemstone, the matching continues with a comparison of the entire gemstone digital pattern of the target gemstone and the corresponding database gemstone digital pattern, resulting in a percentage match of the digital bits for each database gemstone digital pattern as compared to the target gemstone digital patterns.

It has been discovered, according to the present invention, that a very efficient way to store records of gemstones for future verification and authentication is to create a database of derivative information from each known gemstone digital pattern, which includes the area and clockwise angle for the largest spot in each of the concentric bands along with a normalized digital pattern for each of the concentric bands.

It has further been discovered, according to the present invention, that the optimum database for matching each gemstone digital pattern is a database of pre-processed derivative information for each such gemstone created by calculating the radius from the center of each gemstone digital pattern to the center of each spot in such pattern, normalizing each radius to an integer form 0 to 96 and thus creating 96 concentric circle bands beginning at the center of each gemstone digital pattern, calculating the area of each spot in each concentric band and selecting the one spot with the largest area within each concentric band, calculating the clockwise angle of the largest spot in each concentric band relative to the designated origin angle, rotating the gemstone digital pattern counterclockwise by the same angle as the clockwise angle of the largest spot in each concentric band of a digital pattern so that the largest spot is aligned with the origin angle, normalizing the entire gemstone digital pattern also rotated in association with each largest spot in each concentric band down from 512 by 512 pixels to 64 by 64 pixels and storing the information for each gemstone digital pattern, and for each concentric band for such gemstone digital pattern the area and clockwise angle to the origin angle and the rotated and normalized gemstone digital pattern in a relational database associated with each gemstone digital pattern.

It has also been discovered according to the present invention, that the determination of whether a target gemstone is likely to be a specific gemstone from a known database of gemstones can be achieved based on a two phase matching process, the first phase of such process is to compare the pre-processed derivative information associated with the radius of the largest spot, if any, for each concentric band of a digital pattern from the target gemstone with the same pre-processed derivative information of each of the database gemstones, identifying for each database gemstone the match, if any, of the radius of the largest spot, if any, for each concentric band. The second phase of such process is to compare the pre-processed derivative information associated with the rotated and normalized gemstone digital pattern for each concentric band of the target gemstone as applicable with the same pre-processed derivative information for each of the database gemstones and related concentric bands for which there is a match of the radius for any concentric band from the target gemstone with each database gemstone as determined from phase one of such process, resulting in a set of rotated and normalized gemstone digital patterns for each database gemstone-concentric band combination where there is a match of the radius of the target gemstone-concentric band combination with each database gemstone-concentric band combination of the same radius.

It has additionally been discovered, according to the present invention that after the identification of the set of rotated and normalized gemstone digital patterns for each database gemstone-concentric band combination that matches the target gemstone-concentric band combination as described above compares the rotated and normalized target gemstone digital pattern for each concentric band with the selected database gemstone-concentric band digital pattern by overlapping the two digital images and identifying the binary bits in both images that are "on" for the identical x-y coordinates in such images, calculating the percentage match by dividing the matching "on" bits by the smaller of the number of "on" bits from either the target gemstone digital pattern for the relevant concentric band or the database gemstone-concentric band digital pattern that is the subject of the match, and for each database gemstone, identifying the largest percentage match as calculated for each selected gemstone-concentric band combination and storing the largest percentage match in a results list associating each percentage match with an identification ID for each database gemstone for future location.

It is an object of the present invention to generate for each gemstone a derivative set of normalized gemstone digital images wherein the images include a spot pattern generated by a refraction pattern which results from a beam of light transmitted through a gemstone. The set of digital images also includes a rotated and normalized image associated with the largest spot each as applicable in each of 96 concentric bands from each given gemstone digital pattern including the x-y coordinates, a radius and a clockwise angle.

It is a further object of the present invention to provide a method to compare a target gemstone digital image using its derivative information of the normalized radius of the largest spot and the rotated and normalized entire digital image pattern associated with such spot from each of the applicable 96 concentric bands to the pre-processed derivative information of the radius of the largest spot and rotated and normalized digital image pattern associated with such spot from each of the applicable 96 concentric bands related to the database of known gemstone digital images and matching the target gemstone normalized digital image pattern to each of the database gemstone digital normalized image patterns obtaining a percentage match for each of the database gemstone digital images.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
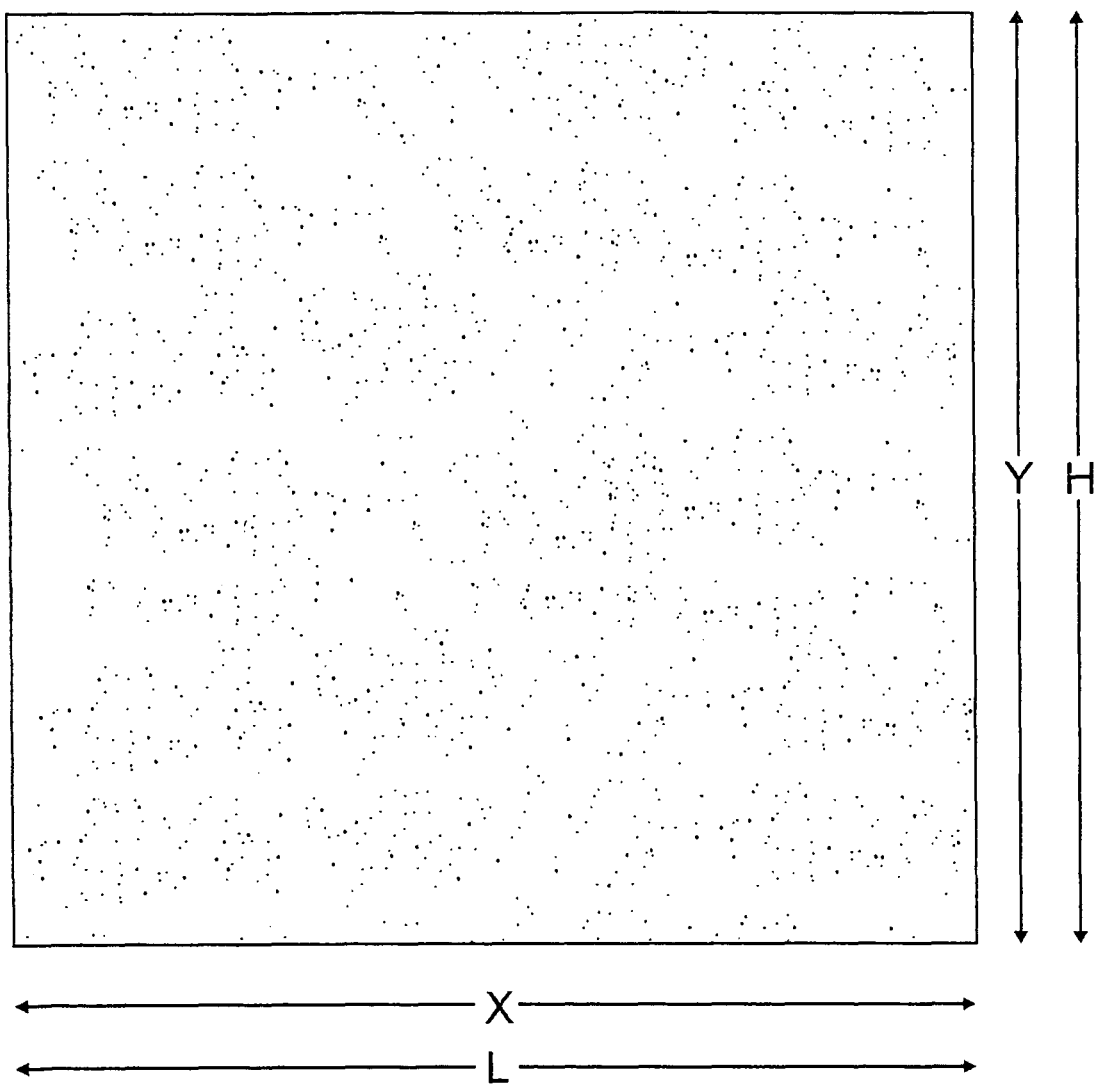
FIG. 1 is a sample gemstone pattern created by transmitting a light beam such as a laser into a gemstone and recording the pattern to obtain a record of the light refraction pattern of that target gemstone.

Referring to FIG. 1, there is illustrated a spot pattern of a gemstone obtained by causing a beam of light such as a laser beam to be transmitted into a gemstone and recording the refractive pattern on a medium which permits a permanent record of the pattern to be created. As illustrated in FIG. 1, the optical pattern of the gemstone is a two dimensional pattern which is comprised of a multiplicity of spots. By way of example, the pattern illustrated in FIG. 1 is a refraction pattern of a laser beam transmitted into a polished diamond. The refraction pattern is projected on a white screen and a digital camera is used to take a picture of the pattern and with associated software the image is stored in a database. By way of example, the optical pattern for each gemstone is a refraction pattern obtained by shining a beam of light into the gemstone and causing the refraction pattern to appear as a two dimensional image which is then photographed and stored.

The two dimensional digital refraction pattern image of the gemstone as illustrated in FIG. 1 has an X axis and a Y axis with a multiplicity of spots of various sizes and shapes and locations at various X-Y positions on the image. The gemstone digital image as depicted in FIG. 1 is monochrome with a length "L" of 512 pixels and a height "H" of 512 pixels.

Figure 2:
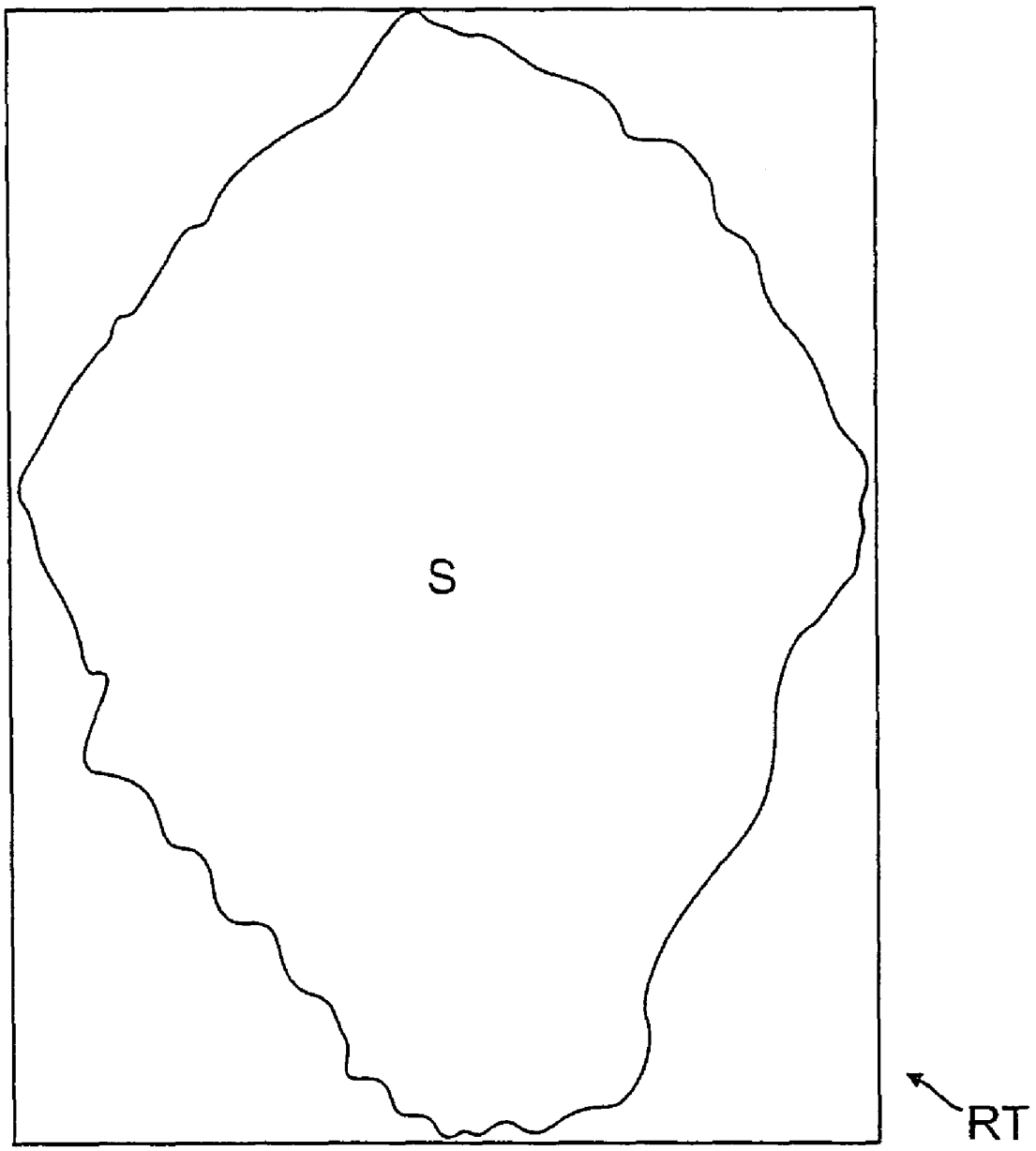
FIG. 2 is an illustration of drawing a rectangle around a spot in the digital gem refraction pattern.
Figure 5A:
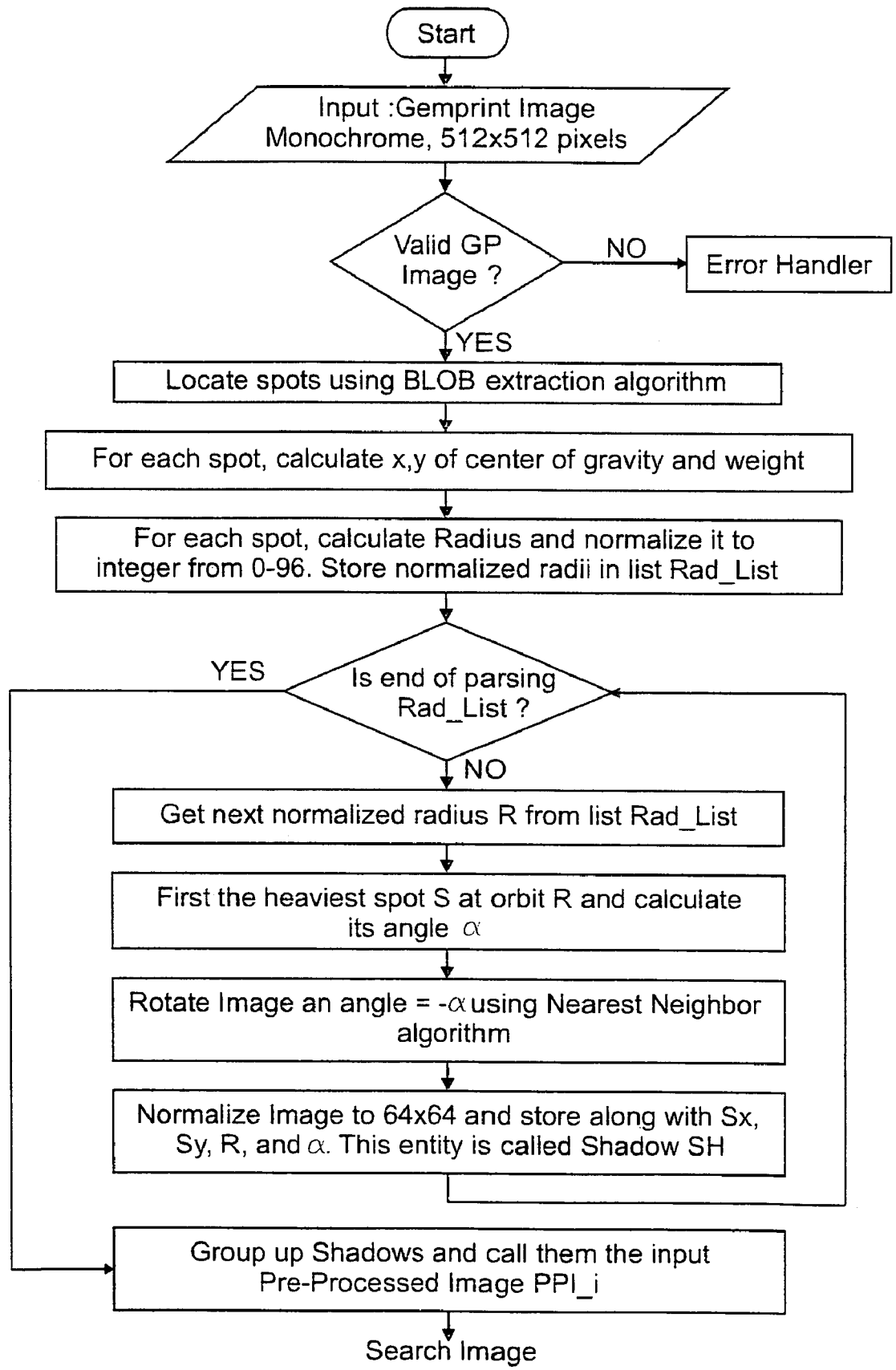
FIG. 5A is a computer flowchart for the present invention method of gemstone pattern recognition technique to calculate the match percentage for each gemstone digital patterns from a database of known gemstones against an input target gemstone digital pattern, with FIG. 5A presenting a flowchart to create a database of pre-processed gemstone images.

Referring to FIG. 2, for each spot "S" of the refraction pattern image as illustrated in FIG. 1, a rectangle "RT" is drawn around the spot. The rectangle "RT" is an attempt to envelope the spot "S" so that the entire spot "S" which has an irregular pattern is within the rectangle "RT". As set forth in the flow chart of FIG. 5A, the first step in the pre-processing routine is to locate each spot in the refraction pattern by using an extraction algorithm. After a rectangle is drawn around each spot in the pattern, a calculation is made to determine the x-y position of the spot on the refraction pattern and in particular the x-y location of the center of gravity and weight of each spot. The center of gravity for a spot is at the center of the rectangle drawn around the spot. The weight is the size of the spot which is approximated as the area of the rectangle drawn around the spot.

Figure 3:
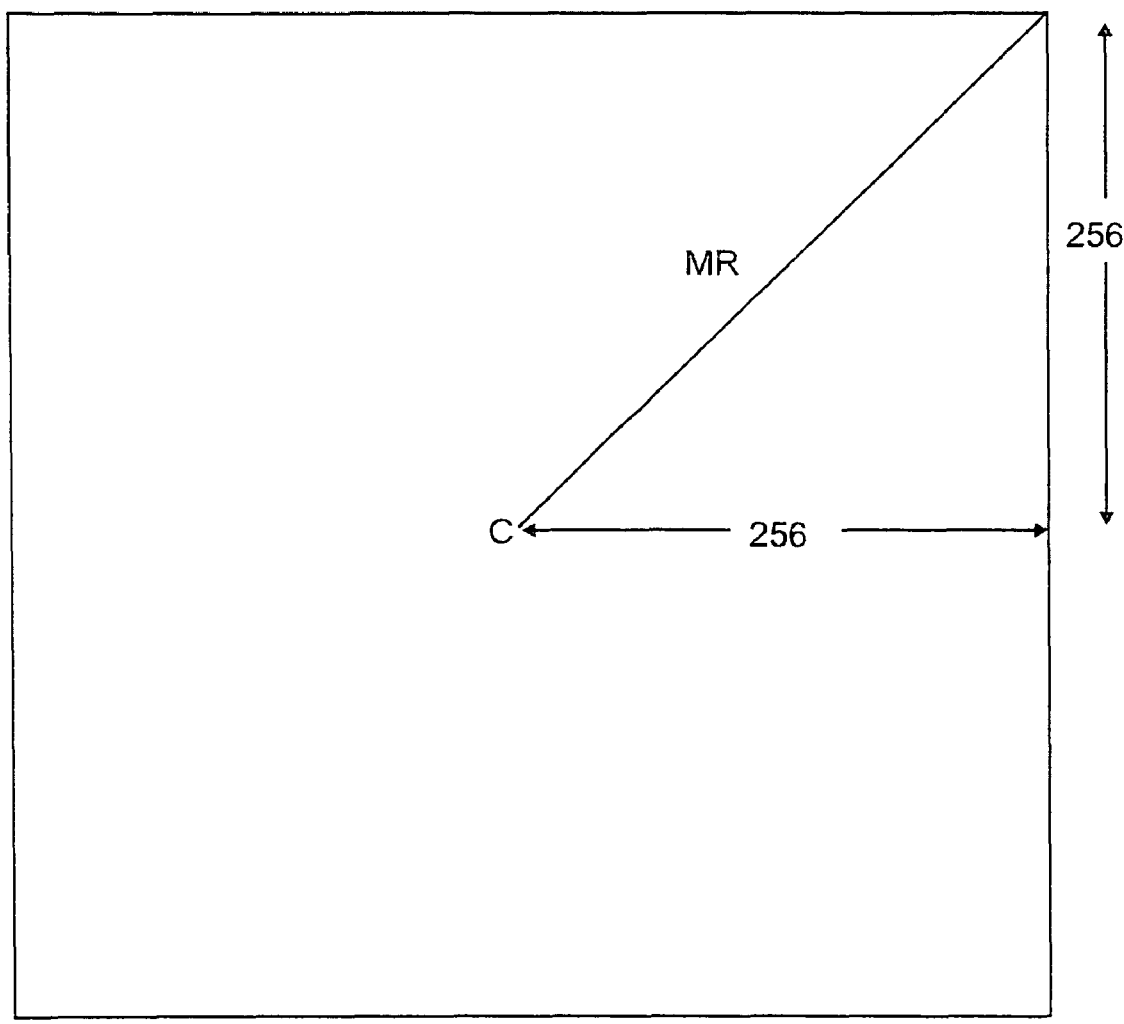
FIG. 3 is an illustration of how the largest radius for the gem pattern is determined.

The maximum radius of the refraction pattern is then determined. Referring to FIG. 3, the maximum radius MR is from the center "C" of the refraction pattern to a corner of the refraction pattern. With the length and height of the refraction pattern each being 512 pixels, the length and height of the center "C" is half this amount or 256 pixels by 256 pixels. The maximum radius is the hypotenuse of the triangle created by the length, height and maximum radius. Using the standard formula "a" squared+"b' squared="c" squared where "a" and "b" are each 256 pixels, the maximum radius is 362 pixels.

Figure 5B:
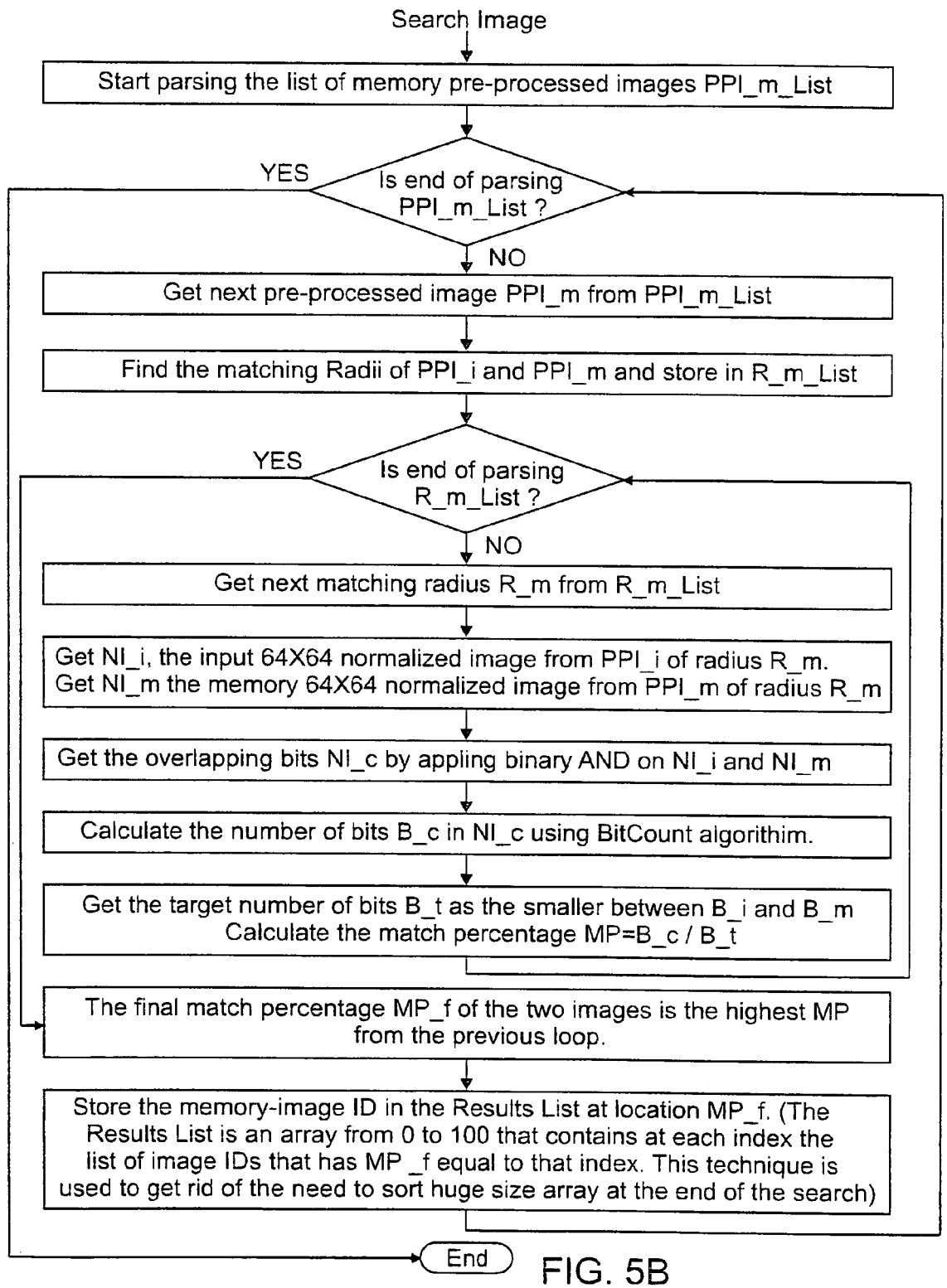
FIG. 5B is a continuation flowchart from FIG. 5A, setting forth the routine to determine the percentage that a target gemstone will match to a database gemstone.

The next step in the routine is to compute the radius for each spot in the refraction pattern wherein the radius of a spot is the distance from the center of the spot to the center "C" of the refraction pattern. Based on the maximum radius, it has been determined that the radii of the spots should be normalized to an integer between 0 and 96. Therefore, after the radius of each spot is calculated, the radius is normalized by dividing the radius by four (4). Referring the FIG. 5, the radius for each spot is calculated and normalized to an integer between 0 and 96, and the normalized radii are stored in a Rad_List.

Figure 4:
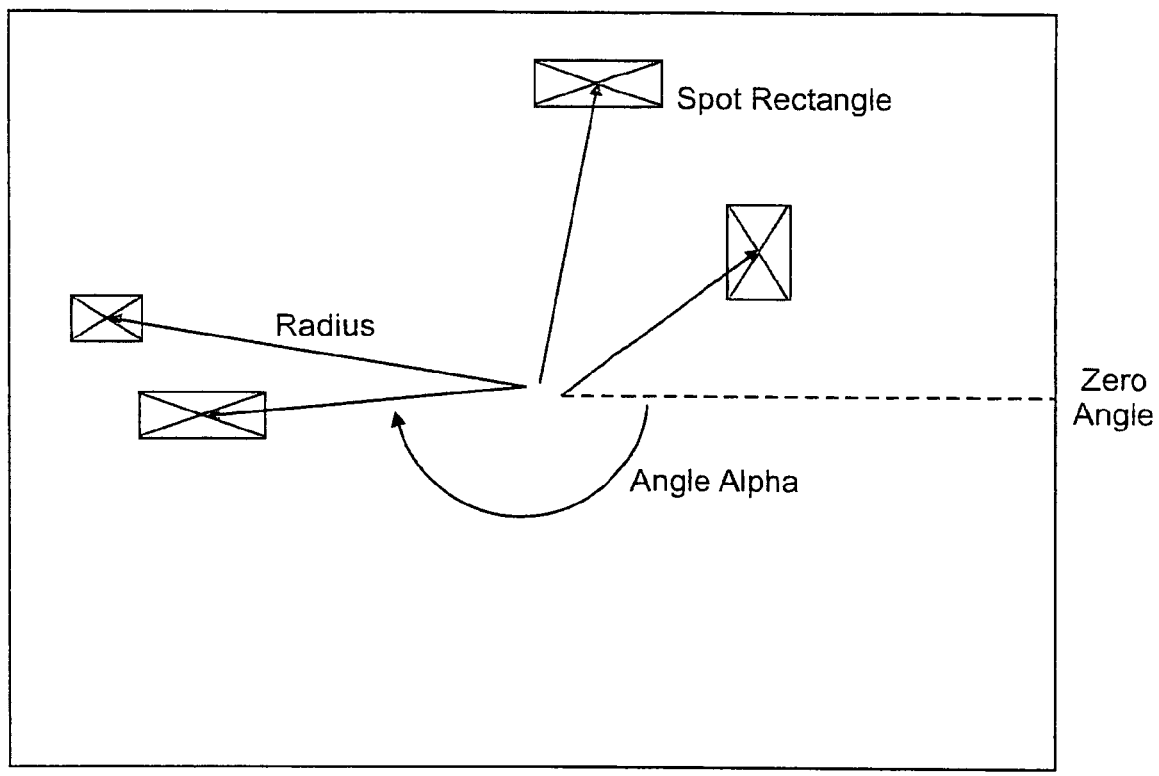
FIG. 4 is an illustration of determining a clockwise angle for a spot in the gem refraction pattern.

After the Rad_List is completed, the next step is to determine the heaviest spot for each radius. The heaviest spot is the one with the largest area rectangle around it. The next step in the routine is to determine the angle of the heaviest spot for each radius. The angle of the spot is relative to a zero angle and the location of the spot based on the radius of the spot relative to the center of the refraction pattern. Referring to FIG. 4, the zero angle is at a 3 o'clock position. The angle alpha (α) is the angle from the zero position clockwise to the location of the spot. For the given refraction pattern of the gemstone being examined, the heaviest spot is located and radius "R" comprising the angle alpha (α) relative to the zero angle. Then using a nearest neighbor algorithm, the image of the entire refraction pattern in a 512×512 pixel image is rotated by the complement of angle alpha (α) so that the heaviest spot is at the zero angle location. Ideally, only the most significant spot or spots are processed in this manner. In theory there could be a maximum of 96 such spots in each refraction pattern but usually there are only 50 or fewer spots processed in this manner for each refraction pattern.

In order to save space, the 512 by 512 pixel image is normalized by dividing each dimension by 8 so that the image size is reduced to 64 by 64 pixels. Then for each radius R the location of the x and y position, of the heaviest spot, the angle alpha ($\alpha$) and the rotated and normalized refraction pattern are stored and referred to as a Shadow Image. The Shadow Images are referred to as the input Pre-Processed Image PPI_i.

To determine the percentage that a target gemstone will match to the database gemstones, the target gemstone Pre-Processed Image is compared to each pre-processed image from the database gemstones in a specified and phased process to maximize the speed of the match. The routine is illustrated on the flow chart of FIG. 5B. The database of all pre-processed images is referred to as PPI_m List as all of the database images are in the computer memory. The matching routine first compares the radius of the target gemstone pre-processed image with each of the Radii of the database gemstone pre-processed images in the memory. The routine finds the matching Radii in PPI_m as compared to PPI_i and stores them in an R_m List. The R_m List is the list of matching Radii from the target gemstone image to the Radii in the memory database of the single database gemstone image for this repetition of this first step.

The next step is to compare the normalized 64×64 pixels images from the target gemstone pre-processed image PPI_i for each of the matching Radii in the R_m List with the corresponding 64×64 pixel images from PPI_m for each matching Radii from the R_m List for the single database gemstone image for this repetition of this second step. In this second step, each 64×64 pixel image associated with a matching Radii from the R_m List from the target gemstone image labeled NI_i and is compared to the 64×64 pixel image associated with the matching Radii from the R_m List from the memory database of the single database gemstone image labeled NI_m. Each of the images NI_i and NI_m contain binary bits which are either "on" or "off". The comparison matches each "on bit" in the same x-y coordinate in both NI_I and NI_M resulting in the matching on bits NI_c and calculating the number of such matching "on bits" as B_c. The percentage of match for each matching Radii, labeled as MP, is calculated by dividing the numerator B_c by the divisor which is the smaller of the total "on bits" in (a) NI_I, labeled as B_i or (b) NI_M, labeled as B_m. The final match percentage, labeled as MP_f, for each single database gemstone image in PPI_m List is the largest MP for all of the matching Radii in R_M List.

The final step is to store the specific identification of a subject from the PPI_m List in an array in a direct association with a fixed reference in the array from 0 to 100 in one unit increments where such fixed reference is equal to the MP_f for each such pre-processed image from the database gemstones as listed in PPI_m List. This technique is used to get rid of the need to sort a huge size array at the end of the search.

The present invention method provides a check that the matching member identification provides confirmation is the subject stone is correlated to a matching image from the database of images of known stones.

The percentage match of the target gemstone image to the known database of gemstone images provides a decision method to determine if the target gemstone is the gemstone sought to be identified for purposes of confirming a stolen gemstone or confirming a valuation for the gemstone. As a general rule, if the final match percentage MP_f is 70% or greater, it is a probable match. If it below 50%, then it probably is not a match.

For purposes of implementing the present invention, the equipment required is an optical scanner and associated software. The hardware can include a PC desktop or laptop with Windows XP or 2000 Pentium III (or equivalent) Processor, 512 MB of RAM, 10 GB of Hard Drive space, although more memory may be required depending on the size of the database of gemstones. Two (2) available USB ports and Internet connectivity.

By way of example, for each specific spot refraction image as illustrated in FIG. 1, the information about the image may include the following information about a gemstone such as a diamond: Polished ID number, Polished weight. The database stored on the server could include the identification number of the company recording the pattern, the Polished ID number, the Polished weight, the date the data was entered and a unique identification number assigned by the software that associates with the specific recorded pattern.

A polished diamond grading document and certificate of authenticity may accompany each gemstone in the database.

Therefore the present invention is a method of providing a pattern recognition technique to determine the percentage match of a target gemstone pattern to a database of known gemstone patterns associated with given gemstones.

Defined generally, the present invention is a method and gem pattern matching technique to analyze a target gemstone comprising: (a) analyzing a pattern of a target gemstone created by transmitting a light source into the gemstone to create a refracted digital pattern and comparing that pattern to a database of known gemstone digital patterns to determine the percentage likelihood that the target gemstone will match a gemstone in the database; (b) the matching is based on an area of a largest spot in each of 96 defined concentric, circular bands of the refracted digital pattern from the target gemstone and a clockwise angle of each of the identified largest spots relative to a designated origin angle in the target gemstone digital pattern and comparing the area and clockwise angle for each concentric band in the target gemstone digital pattern to the area and clockwise angle of the largest spot in each of the 96 concentric bands for each gemstone digital pattern in the database; and (c) upon the occurrence of a match of the area and clockwise angle in a concentric band between the target gemstone and a database gemstone, the matching continues with a comparison of the entire gemstone digital pattern of the target gemstone and the corresponding database gemstone digital patterns, resulting in a percentage match of the digital bits for each database gemstone digital pattern as compared to the target gemstone digital pattern.

Also defined generally, the present invention is a gem pattern matching technique comprising; (a) creating a gemstone database of pre-processed derivative information for each gemstone in the database created by calculating a radius from a-center of each gemstone digital pattern to a center of each spot in such pattern; (b) normalizing each radius to an integer form 0 to 96 and thereby creating 96 concentric circle bands beginning at the center of each gemstone digital pattern; (c) calculating an area of each spot in each concentric band and selecting one spot with the largest area within each concentric band; (d) calculating a clockwise angle of the largest spot in each concentric band relative to a designated origin angle and rotating the gemstone digital pattern counterclockwise by the same angle as the clockwise angle of the largest spot in each concentric band so that the largest spot is aligned with the origin angle; (e) normalizing the entire gemstone digital pattern also rotated in association with each largest spot in each concentric band down from 512 by 512 pixels to 64 by 64 pixels and storing the information for each gemstone digital pattern; (f) storing in the database information on each concentric band for each gemstone digital pattern including the area and clockwise angle to the origin angle and the rotated and normalized gemstone digital pattern associated with each gemstone digital pattern; and (g) comparing information from a target gemstone to the information in the database of gemstones to arrive at a percentage match from the target gemstone to the database of gemstones.

Defined broadly, the present invention is a method to determine whether a target gemstone is likely to be a specific gemstone from a known database of gem stones comprising: (a) a first phase which is comparing pre-processed derivative information associated with a radius of a largest spot, if any, for each concentric band of a digital pattern from a target gemstone with the same pre-processed derivative information of each gemstone in a database of gemstones, identifying for each database gemstone the match, if any, of the radius of the largest spot, if any, for each concentric band; and (b) a second phase which is to compare pre-processed derivative information associated with the rotated and normalized gemstone digital pattern for each concentric band of the target gemstone as applicable with the same preprocessed derivative information for each of the database gemstones and related concentric bands for which there is a match of the radius for any concentric band from the target gemstone with each database gemstone as determined from the first phase, resulting in a set of rotated and normalized gemstone digital patterns for each database gemstone-concentric band combination where there is a match of the radius of the target gemstone-concentric band combination with each database gemstone-concentric band combination of the same radius.

Also defined broadly, the present invention is a gemstone matching technique comprising: (a) generating for each gemstone a derivative set of normalized gemstone digital images wherein the images include a spot pattern generated by a refraction pattern which results from a beam of light transmitted through each gemstone, the set of digital images also including a rotated and normalized image associated with the largest spot for each gemstone in each of 96 concentric bands from each given gemstone digital pattern including the x-y coordinates, a radius and a clockwise angle from a zero reference position, to thereby form a database of information about gemstones; and (b) matching the information from a target gemstone to the database of information about gemstones to determine the percentage match of the target gemstone to a gemstone in the database of digital images.

Defined even more broadly, the present invention is a method of gemstone matching comprising: (a) comparing a target gemstone digital image using its derivative information of a normalized radius of a largest spot, and a rotated and normalized entire digital image pattern associated with the largest spot from each of 96 applicable concentric bands to a pre-processed derivative information of a radius of the largest spot, and rotated and normalized digital image pattern associated with such spot from each of the applicable 96 concentric bands related to a database of known gemstone digital images; and (b) matching the target gemstone normalized digital image pattern to each of the database gemstone digital normalized image patterns and obtaining a percentage match for each of the database gemstone digital images.

Defined in detail, the present invention is a pattern recognition technique to calculate the match percentage of an input gemstone image to a database of known gemstone images, comprising: (a) for each of a multiplicity of gemstones, obtaining an optical pattern which displays a multiplicity of spots on an "x" and "y" monochrome image having a dimension of 512 pixels by 512 pixels, utilizing an extraction algorithm to calculate the "x' and "y" coordinate of each spot, calculating a radius for each spot which is the distance from a center of the image to the center of the spot and calculating the weight of the spot, normalizing the radius for each spot to an integer from 0 to 96 and storing the normalized image in a database, locating the heaviest spot based on weight in each optical image and computing the radius of the heaviest spot and calculating an angle of the heaviest spot relative a horizontal "x" axis, rotating the image by the angle so that the heaviest spot lies along the horizontal "x" axis, normalizing the image to 64 pixels and 64 pixels and storing the x, y, radius and angle location for the heaviest spot in a database, and repeating this process for each gemstone to accumulate a database of pre-processed images; (b) selecting a target gemstone and obtaining an optical image of the target gemstone and comparing the heaviest spot in the target image to the heaviest spots in the pre-processed image data base to locate matching heaviest spots at matching radii, normalizing the matched images to 64 pixels by 64 pixels, converting the matching radii for matching heaviest spot to binary "on" data, calculating the number of "on" bits in the matching radii to generate a matching target bit count and dividing it by the smaller of either the number of input "on" bits or input "off" bits to arrive at a final match percentage for the target and storing the match percentage in a results list and assigning an identification number to that matching percentage; and (c) determining if the match percentage is sufficiently high to determine if the target gemstone matches a gemstone in the database of known gemstones.

Defined more broadly, the present invention is a pattern recognition technique to calculate the match percentage of an input gemstone image to a database of known gemstone images, comprising: (a) for each of a multiplicity of gemstones, obtaining an optical pattern which displays a multiplicity of spots on an "x" and "y" two dimensional image, utilizing an extraction algorithm to calculate the "x' and "y" coordinate of each spot, calculating a radius for each spot which is the distance from a center of the image to the center of the spot and calculating the weight of the spot, locating the heaviest spot based on weight in each optical image and computing the radius of the heaviest spot and calculating an angle of the heaviest spot relative a horizontal "x" axis, rotating the image by the angle so that the heaviest spot lies along the horizontal "x" axis, and storing the x, y, radius and angle location for the heaviest spot in a database, and repeating this process for each gemstone to accumulate a database of pre-processed images; (b) selecting a target gemstone and obtaining an optical image of the target gemstone and comparing the heaviest spot in the target image to the heaviest spots in the pre-processed image data base to locate matching heaviest spots at matching radii, and the matching radii to arrive at a final match percentage for the target and storing the match percentage in a results list and assigning an identification number to that matching percentage; and (c) determining if the match percentage is sufficiently high to determine if the target gemstone matches a gemstone in the database of known gemstones.

Defined even more broadly, the present invention is a pattern recognition technique to calculate the match percentage of an input gemstone image to a database of known gemstone images, comprising: (a) generating a database of normalized gemstone images wherein the images include a spot pattern generated by a refraction pattern which results from a beam of light transmitted through a gemstone, the database including a normalized image for the heaviest spot based on weight in each given gemstone pattern including the location of the heaviest spot, the location being the x and y coordinate of the heaviest spot, the radius from the center of the image to the center of the heaviest spot and the angle of the heaviest spot relative to horizontal, the angle being either in the clockwise or counter-clockwise direction; and (b) providing a method to compare a target gemstone image using the weight and location of its heaviest spot and comparing it to the pre-processed database of images of the heaviest spots of the gemstones in the database and matching the correspondence of the weight of the heaviest spots and their respective locations in each image of the database to the weight of the heaviest spot and location of the heaviest spot in the target image and obtaining a percentage match of the target gemstone image to the gemstone images in the database.

Defined even more broadly, the present invention is a pattern recognition technique to calculate the match percentage of an input gemstone image to a database of known gemstone images, comprising: (a) generating a database of gemstone images wherein the images include a spot pattern in an optical image of the gemstone, the database including an image for the heaviest spot based on weight in each given gemstone pattern including the location of heaviest spot, the location being the x and y coordinate of the heaviest spot, the radius from the center of the image to the center of the heaviest spot and the angle of the heaviest spot relative to horizontal, the angle being either in the clockwise or counter-clockwise direction; and (b) providing a method to compare a target gemstone image using the weight and location of its heaviest spot and comparing it to the pre-processed database of images of the heaviest spots of the gemstones in the database and matching the correspondence of the weight of the heaviest spots and their respective locations in each image of the database to the weight of the heaviest spot and location of the heaviest spot in the target image and obtaining a percentage match of the target gemstone image to the gemstone images in the database.

Defined most broadly, the present invention is a pattern recognition technique to calculate the match percentage of an input gemstone image to a database of known gemstone images, comprising: (a) generating a database of gemstone images wherein the images include a spot pattern in an optical image of the gemstone, the database including an image for the heaviest spot including the location of heaviest spot in the optical image; and (b) providing a method to compare a target gemstone image using the location of its heaviest spot and comparing it to the pre-processed database of images of the heaviest spots of the gemstones in the database and matching the correspondence of the heaviest spots and their respective locations in each image of the database to the location of the heaviest spot in the target image and obtaining a percentage match of the target gemstone image to the gemstone images in the database.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method and gem pattern matching technique to analyze a target gemstone comprising:
    forming a refraction pattern of a target gemstone by transmitting light from a light source into the target gemstone to create the refraction pattern which is recorded on a medium which permits a permanent record of the refraction pattern to be created and stored as an image, wherein the refraction pattern is formed of an arrangement of a multiplicity of spots;
    analyzing the refraction pattern and comparing that refraction pattern to a database of known gemstone refraction patterns to determine the percentage likelihood that the target gemstone matches a known gemstone in the database;
    wherein the step of determining the percentage likelihood that the target gemstone matches a gemstone in the database comprises the steps of:
        calculating a radius (R) for each spot in the refraction pattern, wherein the radius is a distance from a center of the spot to a center of the refraction pattern,
        normalizing the radius (R) for each spot to an integer between 0 and 96 so as to form 96 defined, concentric circular bands of the refraction pattern;
        determining a largest spot, in terms of area, in each of the 96 defined, concentric circular bands of the refraction pattern, wherein a location of the largest spot is determined based on the radius (R) of the spot relative to the center of the refraction pattern;
        determining a clockwise angle of each of the largest spots relative to an origin (zero) angle in the refraction pattern of the target gemstone;
        storing for each radius (R), the location and clockwise angle of the largest spot of the refraction pattern of the target gemstone;
        comparing the stored radii associated with the target gemstone with radii that are stored in the database and associated with known gemstones and generating a list of matching radii;
        for each of the matching radii, the refraction pattern of the target gemstone is compared to the known gemstone refraction patterns by comparing a binary pattern of the refraction pattern of the target gemstone with a binary pattern of each known gemstone refraction pattern, wherein the binary pattern is formed on binary bits that are either "on" or "off" depending upon a presence of the spot therein, with the binary bit being "on" when the spot is present at an x,y location of the respective binary bit;
        determining, for each matching radii, which binary bits are "on", as measured by location, in both the binary pattern of the refraction pattern of the target gemstone and the binary pattern of the known gemstone refraction pattern and thus overlap and thereby represents a matching "on bit" indicative of the presence of the spot at the x,y location of the binary bit;
        calculating a number of matching "on bits" for each matching radii and calculating a percentage of match (MP) of the "on bits" for each matching radii:
        determining a final match percentage (FMP) of the refraction pattern of the target gemstone relative to each of the known gemstone refraction patterns in the database, wherein the final match percentage (FMP) comprises the percentage of match (MP) that has a greatest value relative to all of the percentages of match (MP) for all of the matching radii contained in the list of matching radii; and
        determining a percentage likelihood that the target gemstone matches one known gemstone in the database based on the final match percentage (FMP).

2. The method of claim 1, wherein the step of comparing the refraction pattern of the target gemstone to the known gemstone refraction patterns for each of the matching radii includes the steps of:

rotating the image of the refractive pattern of the target gemstone such that one of the largest spots associated with a respective radius is at a position of the origin (zero) angle; and normalizing the rotated image to create a rotated and normalized refraction pattern and storing an image thereof as a pre-processed input image.

3. The method of claim 2, wherein the step of comparing the stored radii associated with the target gemstone with radii that are stored in the database and associated with known gemstones and generating a list of matching radii comprises comparing the pre-processed input image with each pre-processed image associated with the known gemstones in the database.

4. The method of claim 1, further including the steps of:
drawing a rectangle around each spot in the refraction pattern of the target gemstone so as to completely envelope the spot within the rectangle;
determining an x, y position of the spot; and
determining the center of the spot.

5. The method of claim 4, wherein a weight of each spot is approximately equal to an area of the rectangle drawn around the spot and the largest spot is the spot that is the heaviest in that the area of the rectangle around the spot is greatest along the respective defined concentric circular band.

6. The method of claim 1, wherein the step of calculating the percentage match of the "on bits" (MP) for each matching radii comprises the step of dividing a number of matching "on bits" from either the refraction pattern of the target gemstone for the relevant concentric band or the refraction pattern of one known gemstone that is subject of the match and is stored in the database for the relevant concentric band.

7. The method of claim 1, wherein if the final match percentage is 70% or greater, a probable match exists between the target gemstone and one of the known gemstones in the database.

8. The method of claim 1, wherein the image comprises a monochrome image with a length (L) of 512 pixels and a height (H) of 512 pixels.

9. The method of claim 2, wherein the pre-processed input image has an image size of 64 pixels (length) by 64 pixels (height) as a result of the image of the being normalized.

10. A method and gem pattern matching technique to analyze a target gemstone comprising:
forming a refraction pattern of a target gemstone by transmitting light from a light source into the target gemstone to create the refraction pattern which is recorded on a medium which permits a permanent record of the refraction pattern to be created and stored as an image, wherein the refraction pattern is formed of an arrangement of a multiplicity of spots;
analyzing the refraction pattern and comparing that refraction pattern to a database of known gemstone refraction patterns to determine the percentage likelihood that the target gemstone matches a known gemstone in the database;
wherein the step of determining the percentage likelihood that the target gemstone matches a gemstone in the database comprises the steps of:
calculating a radius (R) for each spot in the refraction pattern, wherein the radius is a distance from a center of the spot to a center of the refraction pattern,
normalizing the radius (R) for each spot to an integer between 0 and 96 so as to form 96 defined, concentric circular bands of the refraction pattern;
determining a largest spot, in terms of area, in each of the 96 defined, concentric circular bands of the refraction pattern, wherein a location of the largest spot is determined based on the radius (R) of the spot relative to the center of the refraction pattern;
determining a clockwise angle of each of the largest spots relative to an origin (zero) angle in the refraction pattern of the target gemstone;
storing for each radius (R), the location and clockwise angle of the largest spot of the refraction pattern of the target gemstone;
comparing the stored radii associated with the target gemstone with radii that are stored in the database and associated with known gemstones and generating a list of matching radii;
for each of the matching radii, the refraction pattern of the target gemstone is compared to the known gemstone refraction patterns by comparing the refraction pattern of the target gemstone with each known gemstone refraction pattern;
calculating a percentage of match (MP) for each matching radii;
determining a final match percentage (FMP) of the refraction pattern of the target gemstone relative to each of the known gemstone refraction patterns in the database, wherein the final match percentage (FMP) comprises the percentage of match (MP) that has a greatest value relative to all of the percentages of match (MP) for all of the matching radii contained in the list of matching radii; and
determining a percentage likelihood that the target gemstone matches one known gemstone in the database based on the final match percentage (FMP).

11. A method to determine whether a target gemstone is likely to be a specific gemstone from a known database of gemstones comprising:
forming a target gemstone digital image by transmitting light from a light source into the target gemstone to create a refraction pattern which is recorded and stored as the digital image, wherein the refraction pattern is formed of an arrangement of a multiplicity of spots, wherein the target gemstone digital image includes derivative information of a normalized radius of a largest spot in terms of area and a rotated and normalized digital image pattern associated with a largest spot from each of 96 concentric circular bands defined in the digital pattern, wherein the normalized radius of the largest spot is calculated by:
calculating a radius (R) for each spot in the refraction pattern, wherein the radius is a distance from a center of the spot to a center of the refraction pattern,
normalizing the radius (R) for each spot to an integer between 0 and 96 so as to form 96 defined, concentric circular bands of the refraction pattern;
determining a largest spot, in terms of area, in each of the 96 defined, concentric circular bands of the refraction pattern, wherein a location of the largest spot is determined based on the radius (R) of the spot relative to the center of the refraction pattern;
wherein the rotated and normalized digital image pattern is generated by:
determining a clockwise angle ($\alpha$) of each of the largest spots relative to an origin (zero) angle in the refraction pattern of the target gemstone; and
rotating the digital image pattern by angle ($\alpha$) so that the largest spot is at the zero angle position;
comparing the target gemstone digital image to a preprocessed derivative information of a radius of a largest spot, in terms of area, and a rotated and normalized digital image pattern associated with the largest spot and a rotated and normalized image pattern associated with the largest spot of the 96 concentric bands related to a database of known gemstone digital images, wherein the normalized radius of the largest spot associated with the pre-processed derivative information is calculated by:

calculating a radius (R) for each spot in the refraction pattern, wherein the radius is a distance from a center of the spot to a center of the refraction pattern, normalizing the radius (R) for each spot to an integer between 0 and 96 so as to form 96 defined, concentric circular bands of the refraction pattern;

determining a largest spot, in terms of area, in each of the 96 defined, concentric circular bands of the refraction pattern, wherein a location of the largest spot is determined based on the radius (R) of the spot relative to the center of the refraction pattern;

wherein the rotated and normalized digital image pattern associated with the pre-processed derivative information is generated by:

determining a clockwise angle ($\alpha$) of each of the largest spots relative to an origin (zero) angle in the refraction pattern of the target gemstone; and rotating the digital image pattern by angle ($\alpha$) so that the largest spot is at the zero angle position; and matching the target gemstone normalized digital image pattern to each of the database gemstone digital normalized image patterns and obtaining a percentage match for each of the database gemstone digital images.

* * * * *